US00PP13548P3

(12) United States Plant Patent
Brown

(10) Patent No.: US PP13,548 P3
(45) Date of Patent: Feb. 4, 2003

(54) MAURANDYA PLANT NAMED 'MAGIC DRAGON'

(76) Inventor: Ray Brown, St. Marychurch Rd., Newton Abbott, South Devon TQ12 4SW (GB)

( * ) Notice: Subject to any disclaimer, the term of this patent is extended or adjusted under 35 U.S.C. 154(b) by 45 days.

(21) Appl. No.: 09/883,420

(22) Filed: Jun. 18, 2001

(65) Prior Publication Data

US 2002/0194658 P1 Dec. 19, 2002

(51) Int. Cl.[7] ..... A01H 5/00
(52) U.S. Cl. ..... Plt./226
(58) Field of Search ..... Plt./226

(56) References Cited

PUBLICATIONS

"Maurandya antirrhiniflora Snapdragon Vine" http://www-.laspilitas.com/plants/430.htm.*

Brown, Ray "New Introductions for 1997" Plants Magazine, Issue 7 wysiwyg://9/http://www.plants–magazine.com/articles/article108.shmtl.*

"Asarina_erubescens_lien" http://www.barbidine.com/pages/assarina_erubescens_lien.htm.*

* cited by examiner

*Primary Examiner*—Bruce R. Campell
*Assistant Examiner*—W C Haas
(74) *Attorney, Agent, or Firm*—Mark P. Bourgeois

(57) ABSTRACT

A new cultivar of Maurandya named 'Magic Dragon' that is characterized by semi-weeping branches and light green foliage, large bright red trumpet-shaped flowers with flared lobes, and a climbing habit when secured to a stake or trellis. In combination these traits set 'Magic Dragon' apart from all other existing varieties of Maurandya.

2 Drawing Sheets

BOTANICAL CLASSIFICATION

Maurandya hybrid.

BACKGROUND OF THE INVENTION

The present invention relates to a new and distinct cultivar of Twining Snapdragon known botanically as Maurandya and referred to hereinafter by the cultivar name 'Magic Dragon'. The present invention was selected by the inventor in July 1995 in Newton Abbot, United Kingdom. The new invention is the product of the inventors breeding program. The purpose of the program was to produce a plant that will exhibit a climbing habit, while producing the bright red flowers of 'Red Dragon' and the larger flared trumpet flowers of *Maurandya erubescens.*

'Magic Dragon' is a hybrid that resulted from the induced hybridization of the female parent Maurandya 'Red Dragon' (not patented) and the male parent *Maurandya erubescens* (not patented). Correct nomenclature listed in The Royal Horticultural Society Dictionary of Gardening for Maurandya 'Red Dragon' includes the synonym Asarina 'Red Dragon' and correct nomenclature for *Maurandya erubescens* includes the synonym *Asarina lophospermum.*

'Magic Dragon' is distinguished by light green foliage, increased vigor over the parent plants, a climbing habit when secured to a stake or trellis, and large bright red, trumpet-shaped flowers with flared lobes. The closest comparison plants are the parents. 'Magic Dragon' differs from 'Red Dragon' in its climbing habit when secured and larger flared trumpet flowers. 'Magic Dragon' is distinguishable from *Maurandya erubescens* by the bright red color of its flowers.

'Magic Dragon' was first asexually propagated by the inventor in Newton Abbot, England in June 1996. Asexual propagation was accomplished using vegetative tip cuttings. Since that time, under careful observation, successive generations have been determined fixed, stable and uniform.

SUMMARY OF THE INVENTION

The following represent the distinguishing characteristics of the new Maurandya cultivar 'Magic Dragon'. In combination these traits set 'Magic Dragon' apart from all other existing varieties of Maurandya. 'Magic Dragon' has not been tested under all possible conditions and phenotypic differences may be observed with variations in environmental, climatic, and cultural conditions, however, without any variance in genotype.

1. Maurandya 'Magic Dragon' exhibits semi-weeping branches and light green foliage.
2. Maurandya 'Magic Dragon' exhibits large, flared, bright red trumpet-shaped flowers.
3. Maurandya 'Magic Dragon' exhibits a climbing habit when secured to a stake or trellis.
4. Maurandya 'Magic Dragon' is 2 meters in height at maturity.
5. Maurandya 'Magic Dragon' is hardy to USDA Zone 9.
6. Maurandya 'Magic Dragon' blooms in spring and summer.

BRIEF DESCRIPTION OF THE DRAWINGS

The accompanying color photographs illustrate the distinguishing traits of 'Magic Dragon'. The plants in the photographs are ten months old and were grown outside in fifteen-gallon containers.

The photograph on sheet 1 illustrates an entire specimen of 'Magic Dragon' in bloom from a side perspective.

The photograph on sheet 2 is a close-up photograph illustrating the flower and leaf. All photographs are taken using conventional techniques and although foliage colors may appear different from actual colors due to light reflectance, they are as accurate as possible by conventional photography.

BOTANICAL DESCRIPTION OF THE PLANT

The following is a detailed description of the Maurandya cultivar named 'Magic Dragon'. Data was collected in Arroyo Grande, Calif. from ten month old plants grown outside in five-gallon containers. Color determinations are in accordance with The Royal Horticultural Society Colour Chart except where general color terms of ordinary dictionary significance are used. The growing requirements are similar to the species and no disease problems have been observed.

Botanical classification: Maurandya 'Magic Dragon'.
Common name: Twining snapdragon.
Use: Ornamental container vine or trellis.
Parentage: Maurandya 'Magic Dragon' is the result of an induced hybridization between the following plants:
*Female parent.*—Maurandya 'Red Dragon'.
*Male parent.*—*Maurandya erubescens.*
Growth rate: Vigorous to aggressive.
Growth habit: Scandent when secured to a stake or trellis.
Height: 2 meters or more in height at maturity.
Width: 40–60 cm. in width.
Hardiness: USDA Zone 9.
Propagation: Propagated by vegetative tip cuttings.
Root system: Fibrous.
Cultural requirements: Plant in well-drained soils and full sunlight.
Type: Perennial.
Time to initiate roots: 2–3 weeks are required at 25° Centrigrade for cuttings to root.
Time to develop to a five-gallon container: 3–4 months is required to develop a finished five-gallon container from a rooted cutting.
Branching habit: Semi-weeping.
Seasonal interest: Large bright red flowers in spring and summer.
Stem:
*Stem shape.*—Cylindrical.
*Dimensions of stem.*—To 0.25 cm. wide and 35 cm. in length.
*Internode length.*—1.5 to 3 cm. between nodes.
*Stem diameter.*—2.5 cm. in diameter.
*Stem length.*—10.5 cm. in length.
*Surface.*—Tomentose and glandular with beads of sticky fluid.
*Color of tomenta.*—197B.
*Color of stem.*—146C.
Foliage:
*Type.*—Evergreen.
*Leaf arrangement.*—Alternate.
*Leaf division.*—Simple.
*Leaf shape.*—Deltoid.
*Leaf base.*—Sagitate.
*Leaf tip.*—Aristulate.
*Leaf venation.*—Palmate with three prominent veins protruding on the abaxial surface and three veins depressed on the adaxial surface.
*Vein color* (*adaxial and abaxial surface*).—144D.
*Leaf surface* (*adaxial*).—Tomentose and glandular with beads of sticky fluid.
*Leaf surface* (*abaxial*).—Tomentose and glandular with beads of sticky fluid.
*Leaf attachment.*—Petiolate.
*Petiole dimensions.*—2 mm in width and 1.5–2 cm. in length.
*Petiole surface.*—Heavily pubescent.
*Color of petiole.*—199B.
*Leaf margin.*—Biserrate.
*Leaf length.*—4 cm in length.
*Leaf width.*—3.5–4 cm in width.
*Quantity of leaves.*—Approximately 17 leaves per stem.
*Leaf color* (*adaxial and abaxial surface*).—144A.
*Foliar fragrance.*—None observed.
Flower:
*Form.*—Solitary.
*Flower arrangement.*—Axillary.
*Shape of flower.*—Tubular to trumpet with flared lobes and exhibiting a tumid region on the ventral basal surface of the corolla tube.
*Flower symmetry.*—Irregular and bilabiate.
*Sexuality.*—Bisexual.
*Dimensions of nectary.*—2.5 cm. in length and 1–2 cm. in width.
*Color of nectary.*—15A.
*Surface of nectary.*—Bearded.
*Region of nectary.*—Two rows running lengthwise along the ventral basal surface of the corolla tube.
*Flower aspect.*—Facing outward.
*Color of flower petal.*—185A with tint of 64B on the lobes.
*Petals.*—Five in number.
*Petal surface.*—Smooth surface.
*Dimensions of corolla tube.*—5 cm. in length and 3 cm. in diameter.
*Corolla lobes.*—Five in number.
*Dimensions of lobes.*—Each lobe is 1.5 cm. in width and 1 cm. in length.
*Color of corolla tube.*—185A.
*Petals unfused or fused.*—Sympetalous.
*Bud color.*—185A.
*Bud dimensions.*—3 cm. in length and 1 cm. in width.
*Persistent or self-cleaning.*—Self-cleaning.
*Shape of calyx.*—Tubular when closed and stellate when open.
*Color of calyx.*—144A.
*Dimensions of calyx.*—3 cm. in length and 2.5 cm. in diameter.
*Number of sepals.*—Five sepals basally united.
*Sepal color.*—144A.
*Blooming period.*—Spring and summer.
*Peduncle dimensions.*—2 mm. in width and 3.5 cm. in length.
*Color of peduncle.*—199A.
*Surface of peduncle.*—Stipitate glandular surface.
*Fragrance.*—None observed.

Reproduction organs:

*Stamens.*—Four in number that rest against the ventral surface of the corolla tube opposite the nectary.

*Form of stamen.*—Included.

*Color of filament.*—155B suffused with 59C at base.

*Dimensions of stamen.*—2.5–3 cm. in length and 1 mm in diameter.

*Arrangement of stamens.*—Didynamous.

*Anther type.*—Adhering.

*Anther color.*—155B.

*Dimensions of anther.*—3 mm. in width and 3 mm. in length.

*Pollen color.*—158D.

*Amount of pollen.*—Moderate.

*Pistil.*—One in number.

*Pistil color.*—157A.

*Dimensions of pistil.*—4.5–5 cm. in length and less than 0.50 mm. in diameter.

*Form of stigma.*—Stigmas are united.

*Stigma color.*—161A.

*Dimensions of stigma.*—1 mm. in height and 1.25 mm. in diameter.

*Style color.*—155D.

*Style dimensions.*—1 mm. in length and less than 0.50 mm. in diameter.

*Ovary position.*—Superior.

*Ovary color.*—145CB.

*Ovary dimensions.*—2 mm. in diameter and 1 mm. in height.

*Ovary shape.*—Globose.

Seed: Seed production has not been observed.

I claim:

1. A new and distinct variety of Maurandya plant named 'Magic Dragon' as illustrated and described.

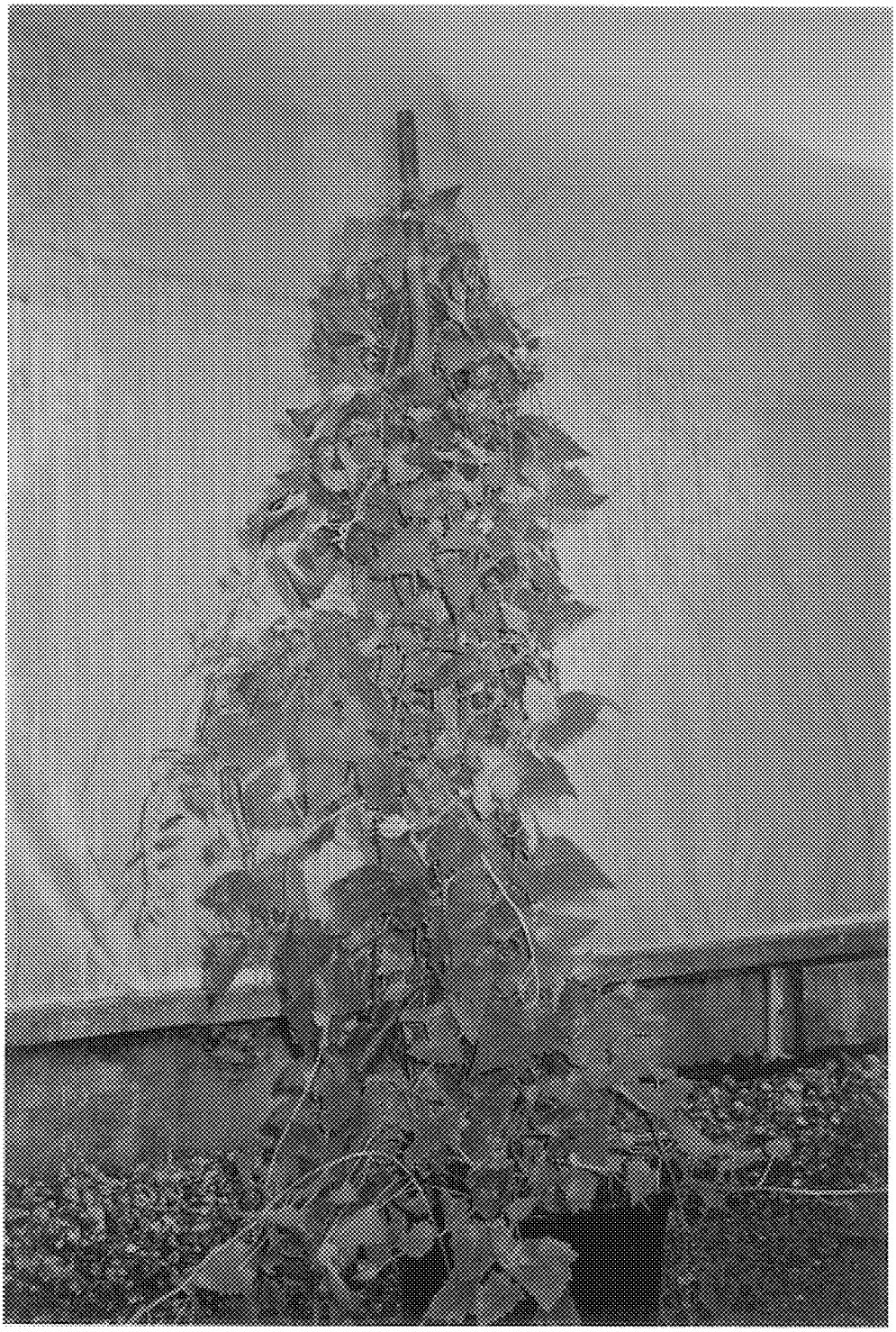

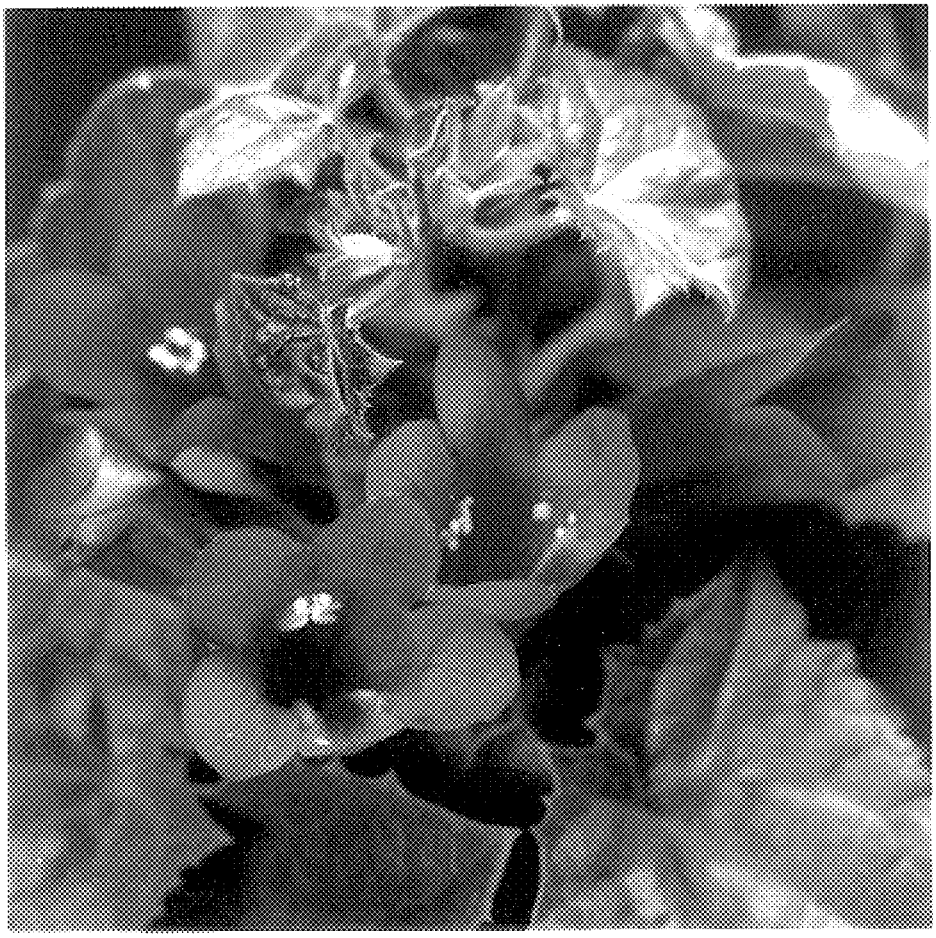

* * * * *